United States Patent [19]

Skidmore et al.

[11] Patent Number: 4,807,636

[45] Date of Patent: Feb. 28, 1989

[54] METHOD AND APPARATUS FOR MEASURING VOLUME FLUID FLOW

[75] Inventors: R. Skidmore; Jonathan M. Evans, both of Bristol, England

[73] Assignee: Vital Science Corporation, Englewood, Colo.

[21] Appl. No.: 905,742

[22] Filed: Sep. 9, 1986

[51] Int. Cl.$^4$ .............................................. A61B 10/00
[52] U.S. Cl. .............................. 128/661.10; 73/861.25
[58] Field of Search ............................... 128/660–663; 73/861.25; 367/90

[56] References Cited

U.S. PATENT DOCUMENTS

| | | | |
|---|---|---|---|
| 3,498,290 | 3/1970 | Shaw et al. | 128/663 |
| 3,554,030 | 1/1971 | Peronneau | 128/663 X |
| 3,977,247 | 8/1976 | Hassler | 73/861.25 |
| 4,060,763 | 11/1977 | Hassler | 73/861.25 X |
| 4,062,237 | 12/1977 | Fox | 73/861.25 |
| 4,067,236 | 1/1978 | Hottinger | 73/861.25 |
| 4,155,259 | 5/1979 | Engeler | 128/660 X |
| 4,155,260 | 5/1979 | Engeler et al. | 128/660 X |
| 4,257,278 | 3/1981 | Papadofrangakis et al. | 73/861.25 |
| 4,431,936 | 2/1984 | Fu et al. | 310/335 |
| 4,493,216 | 1/1985 | Hassler | 73/861.25 |
| 4,530,363 | 7/1985 | Brishen | 128/663 |
| 4,534,357 | 8/1985 | Powers | 128/663 |
| 4,541,437 | 9/1985 | Amemiya | 128/663 |
| 4,593,700 | 6/1986 | Hayakawa et al. | 128/663 |

Primary Examiner—Francis J. Jaworski
Attorney, Agent, or Firm—Sheridan, Ross & McIntosh

[57] ABSTRACT

A system is provided for measuring volume blood flow using non-invasive ultrasonic Doppler techniques. This system includes a probe assembly including a transducer having an inner transducer element and a concentric outer transducer element. A wide beam of ultrasonic energy is transmitted using the transducer and is received by a lumen area. Reflected untrasonic energy is returned to the transducer. Both the outer and inner transducer elements of the transducer are used to generate signals representative of a wide beam and a narrow beam. These generated signals include Doppler information. The signals representative of the wide beam are processed simultaneously with signals representative of the narrow beam to produce Doppler power spectrums associated with the wide and narrow beams. Phase quadrature signals are also generated for use in determining the direction of blood flow at the insonified lumen area. An AGC circuit is utilized for controlled amplitude fluctuations in the wide beam Doppler power spectrum. The control signal is also applied to the narrow beam power spectrum to avoid the introduction of inaccuracies in the subsequent computation of the ratio of wide beam power to narrow beam power. A mean frequency estimator circuit is also provided for determining the velocity of the blood flow at the insonified lumen area. The determined flow velocity is applied to a recording device for observation by the operator. The operator relies on the flow velocity trace in ensuring correct placement of the probe assembly for insonifying a desired lumen area. After it has been determined that the probe assembly is properly located, a processing-/controlling unit determines volume blood flow by multiplyng the determined flow velocity by the ratio of the obtained powers in the wide and narrow beams.

25 Claims, 5 Drawing Sheets

METHOD AND APPARATUS FOR MEASURING VOLUME FLUID FLOW

FIELD OF THE INVENTION

The present invention relates to systems for determining volume fluid flow and, in particular, to a measuring apparatus that determines volume blood flow in a non-invasive manner.

BACKGROUND INFORMATION

The monitoring of volume blood flow through a vessel or other conduit of a patient is important for a number of reasons. During surgery, it is beneficial to monitor blood flow of the patient, among other vital signs that are monitored, to enhance the safety of the patient. Cardiovascular disorders can be better diagnosed and assessed through observation and study of volume blood flow. Restricted volume blood flow, including the degree thereof, is indicative of some form of cardiovascular disease. Flow measurements are also important when there has been a loss of blood and when the body has been subject or exposed to infection, metabolic disease, and unwanted drug/anesthetic effects.

Techniques have been previously devised for measuring volume blood flow. Traditional methods include invasive steps in which there is some disruption or alteration of the vascular system to be measured. Invasive approaches are unsuitable for a variety of reasons, including patient discomfort, greater risk because of the invasive steps that are required, and the need to use sterilized and expensive, non-reusable medical devices, such as catheters.

To overcome the drawbacks associated with invasive techniques, non-invasive methods have been advanced. These systems typically rely on the use of ultrasound and Doppler techniques. Basically, the velocity of the blood flow through a lumen is determined and that is multiplied by the cross-sectional or projected area of the lumen at the point of interest to determine volume blood flow.

A number of different approaches have been developed or proposed for determining volume blood flow. In U.S. Pat. No. 4,067,236 to Hottinger, issued Jan. 10, 1978, and entitled "Method and System for Unambiguous Measurement of Volume Flow," a Doppler system is disclosed in which flow velocity is determined as a function of the centroid or first moment of the Doppler power spectrum. In one embodiment disclosed in this patent, the lumen projected area is found using the ratios of returned Doppler power from two transducer elements. Circuitry is also described for providing information relating to the direction of blood flow. U.S. Pat. No. 4,431,936 to Fu et al., issued Feb. 14, 1984, and entitled "Transducer Structure for Generating Uniform and Focused Ultrasonic Beams and Applications Thereof" describes a transducer arrangement that, in one embodiment, includes outer and inner array elements for use in generating a wide beam and a narrow beam of ultrasonic energy. The Doppler information returning from the vessel of interest is used in determining volume blood flow. Another method for measuring flow volume that relies on a pair of transducer elements is found in U.S. Pat. No. 3,977,247 to Hassler, issued Aug. 31, 1976, and entitled "Arrangement for the Measurement of the Flow Volume of Flowing Media." The Hassler patent determines the lumen area of interest by using Doppler power associated with generated wide and narrow beams. The system disclosed in this patent also includes an indicator for displaying Doppler power signals from either the wide or narrow beam at any one time so that the highest intensity Doppler signal can be observed indicating that the narrower beam is passing through the blood vessel at the cross-sectional middle thereof. Further systems for measuring volume fluid flow using Doppler information are U.S. Pat. No. 4,062,237 to Fox, issued Dec. 13, 1977, and entitled "Cross Beam Ultrasonic Flowmeter," U.S. Pat. No. 3,554,030 to Peronneau, issued Jan. 12, 1971, and entitled "Recording Ultrasonic Flowmeter for Blood Vessels," and U.S. Pat. No. 3,498,290 to Shaw et al., issued Mar. 3, 1970, and entitled "Pulsed Doppler Volumetric Blood Flowmeter." These patents reveal various circuit elements and arrangements thereof for processing the received Doppler input including the use of multiplying circuits, band pass filters, amplitude limiters, and range gating circuitry. Another apparatus for measuring blood flow velocity is described in U.S. Pat. No. 4,593,700 to Hayakawi et al., issued June 10, 1986, and entitled "Ultrasonic Wave Blood Flow Meter." The disclosed apparatus includes orthogonal phase detection circuitry for providing Doppler information signals which have their phases shifted by 90° from each other.

Despite the variety of systems that have been devised and which rely on non-invasive techniques, drawbacks to the use of such systems in a clinical environment still exist. In that regard, a volume blood flow measuring system that incorporates the features of providing highly accurate volume fluid flow-related measurements, while being relatively inexpensive and easy to use would be very beneficial to medical diagnosticians and others interested in obtaining information relating to volume fluid flow.

SUMMARY OF THE INVENTION

In accordance with the present invention, a clinically effective apparatus is provided for monitoring and measuring volume blood flow through a vessel or lumen located in the body of a patient. The apparatus includes a probe assembly for transmitting and receiving ultrasonic energy. The probe assembly includes a two-element transducer in which an outer transducer element is concentrically located relative to an inner transducer element. The transmission and reception by the transducer of ultrasonic energy is controlled using a processing/controlling unit that operatively communicates with the transducer using clock signals, amplifiers, and desired logic gates. In one embodiment, and unlike known prior art, the two-element transducer is uniquely configured to produce a 3 cm wide beam at 6 cm from the outer face of the probe assembly when the transducer elements are energized using a 2 MHz signal. In this configuration, the transducer includes an inner element and an outer element. The inner transducer element is a 2 mm disk and the outer transducer element is an annulus having a width of about 2 mm and being located about the outer periphery of the inner disk. This particular transducer is used in measuring volume blood flow through the ascending aorta. To transmit ultrasonic energy, a wide beam is generated by simultaneously energizing the outer and inner elements of the transducer. The transmitted energy is directed to the lumen of interest and the lumen reflects ultrasonic energy whereby returned energy is received by the transducer. The returned energy is defined in the form of a wide beam of energy and a narrow beam of energy using electrical signals generated by the transducer. The wide beam includes energy received by the inner transducer element and energy received by the outer transducer element. Similarly, the narrow beam includes energy received by the inner element and energy received by the outer element of the transducer. Both beams are received at the same time and simultaneously applied to demodulating circuitry. In contrast to known prior art, both the returned wide beam and narrow beam signals are demodulated or processed at the same time so that there is no delay between processing Doppler information from the wide beam and processing of Doppler information from the narrow beam.

In one embodiment, the demodulating circuitry includes eight channels, with each of the circuit channels including a multiplier circuit. Returned ultrasonic energy, including Doppler signal information, received by the inner transducer element is inputted to four of the multiplier circuits, while returned ultrasonic energy, including Doppler signal information, received by the outer transducer element is inputted to the other four multiplier circuits. Each of the multiplier circuits also receives a clock signal of a predetermined frequency and phase. For each multiplier circuit, each clock signal is multiplied or mixed with the inputted signal representative of received ultrasonic energy to output sums and differences of the two inputted signals. Four of the clock signals are provided to multiplier circuits in order to generate phase quadrature signals. The quadrature signals are phase shifted 90° relative to the normal or direct signals. The quadrature signals are used in determining the direction of the blood flow, i.e., whether the flow is towards or away from the probe assembly.

There is further processing of the received ultrasonic energy including the Doppler signal information whereby the two signal components representative of the wide beam are added or combined while the two signal components representative of the narrow beam are combined. The two wide beam quadrature signals and, similarly, the two narrow beam quadrature signals are also combined. The combined signals are applied to depth selection circuits and filter circuits to output Doppler signals or Doppler power spectrums representative of the difference between the frequency of transmitted energy and received energy. In the preferred embodiment, the normal and quadrature signals representative of the wide beam Doppler signals are sent to an AGC circuit. The AGC circuit reduces the amplitude fluctuations present in the Doppler signals. The widely varying signal amplitudes are caused by the scattering effect of the ultrasonic energy, which is due to the random collection of red blood cells being insonified. Because it is necessary to determine the ratio of the Doppler power in the wide beam to the Doppler power in the narrow beam, the effect of the use of the AGC circuit in the wide beam channel must be compensated for in the narrow beam channel. This is accomplished by using a feedback control signal to modify the power in the narrow beam that is the same as that being used to maintain a consistent signal amplitude for the wide beam. After the amplitudes of the Doppler signals have been adjusted, the power in the wide beam and the power in the narrow beam are determined. Each of the determined power outputs are then inputted to the processing/controlling unit for use in determining the ratio of the two power values. The ratio of the power from the wide beam to the power n the narrow beam is indicative of the cross-sectional area of the insonified lumen. In addition to determining the power output of the Doppler signals of the wide and narrow beams, the flow velocity of the blood is determined by means of a mean frequency estimator circuit which receives, as its inputs, the normal and phase quadrature signals of the Doppler power spectrum for the wide beam. The mean frequency that is determined by this circuit is directly proportional to the velocity of the blood at the insonified lumen area. The determined flow velocity is applied to a recording device which displays a signal representative of the flow velocity of the blood. In contrast to known systems, the trace or graph of the flow velocity is used in positioning the probe assembly on the patient's body to accurately measure blood volume flow. That is, the operator or user observes the trace of the flow velocity and, when a known or predetermined flow velocity trace is observed, the operator knows that the probe assembly is correctly positioned. Once the proper position of the probe assembly is achieved, the processing/controlling unit can then calculate volume blood flow with a high degree of accuracy by multiplying the current flow velocity by the ratio of the determined power Doppler outputs for the wide and narrow beams.

In view of this summary, a number of salient features of the present invention are easily recognized. The disclosed apparatus provides a workable implementation of generally theoretical studies and efforts in the area of measuring volume fluid flow. The apparatus of the present invention can be used in a clinical environment and incorporates techniques and features that achieve this principal objective. Circuitry is provided for simultaneously computing Doppler power from a wide beam and a narrow beam so that there is certainty that the power in the wide beam and the power in the narrow beam are determined during the time that the transducer is insonifying the exact same lumen area. Consequently, inadvertent movement of the probe assembly by the operator does not result in a determination of wide beam power for a different lumen area than the area for which the narrow beam power was found. The apparatus includes circuitry for generating phase quadrature signals in order to determine the direction of flow of the blood in the vessel of interest. Additionally, circuitry is provided to reduce amplitude fluctuations caused by the returned Doppler signals without adversely affecting the determination of the ratio of the power in the wide beam to the power in the narrow beam. A recording device is also provided so that the operator can observe the flow velocity trace in order to ensure that the probe assembly is correctly placed for accurately determining volume blood flow. Lastly, in one embodiment for monitoring and measuring volume blood flow in the ascending aorta, a uniquely configured probe assembly is utilized wherein the wide beam is produced having a desired width at a selected depth.

Additional advantages of the present invention will become readily apparent from the following discussion, when taken in conjunction with the accompanying drawings.

DETAILED DESCRIPTION OF THE PREFERRED EMBODIMENTS

Figure 1:
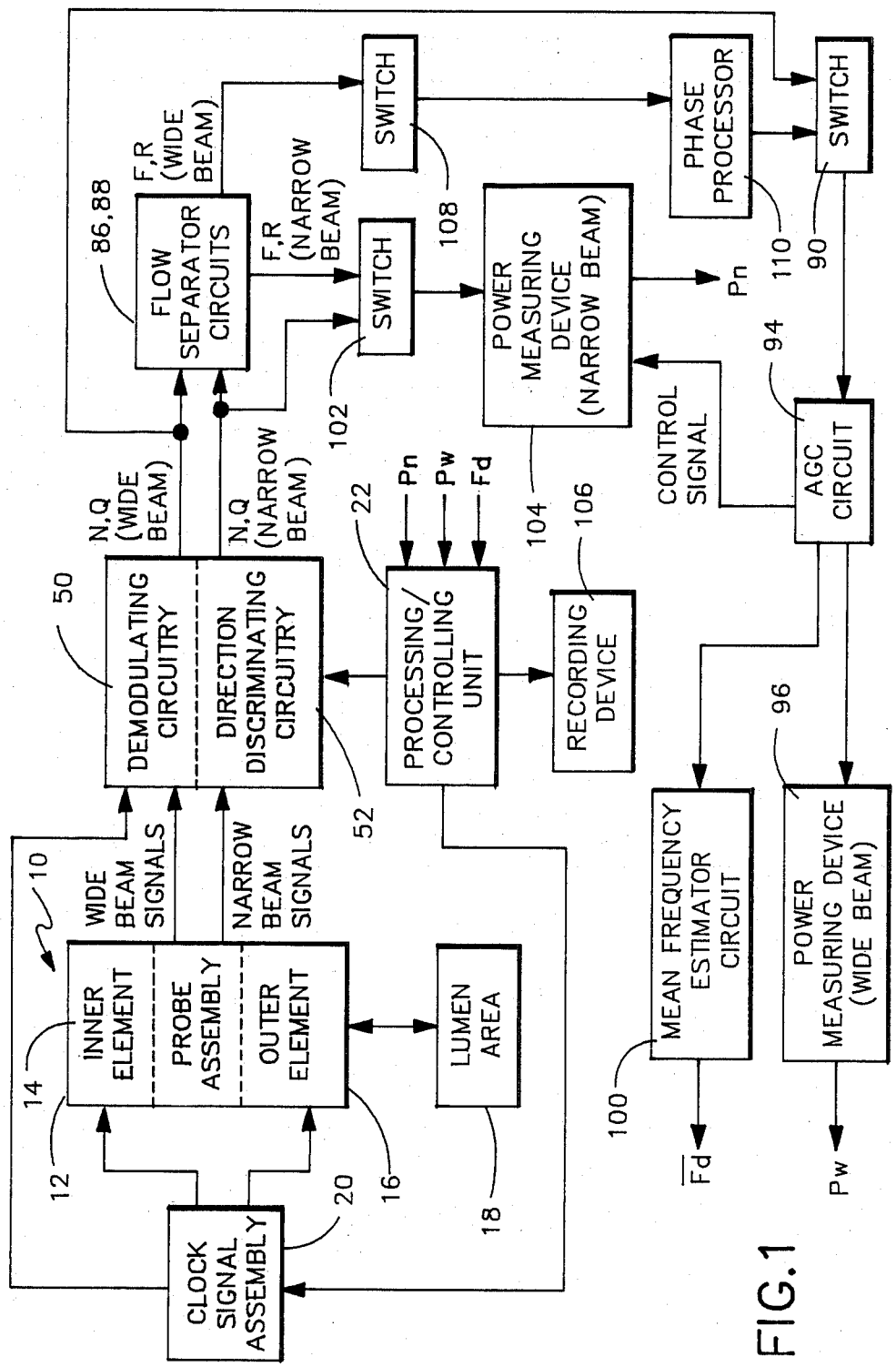
FIG. 1 is a block diagram of the present invention.
Figure 2A:
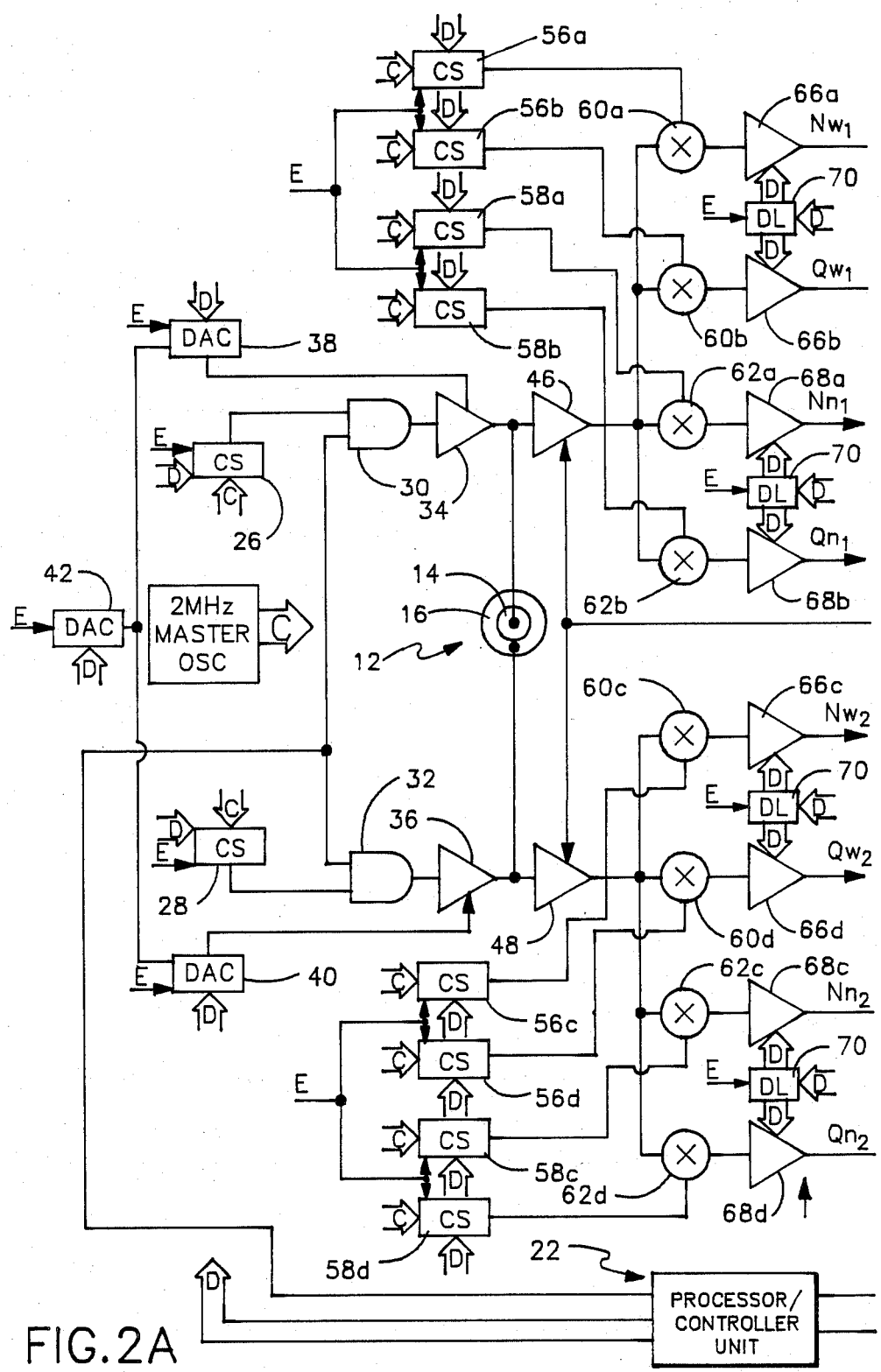
FIGS. 2A and 2B are further block diagram of the present invention diagramatically illustrating additional detail of the hardware of the present invention.
Figure 2B:
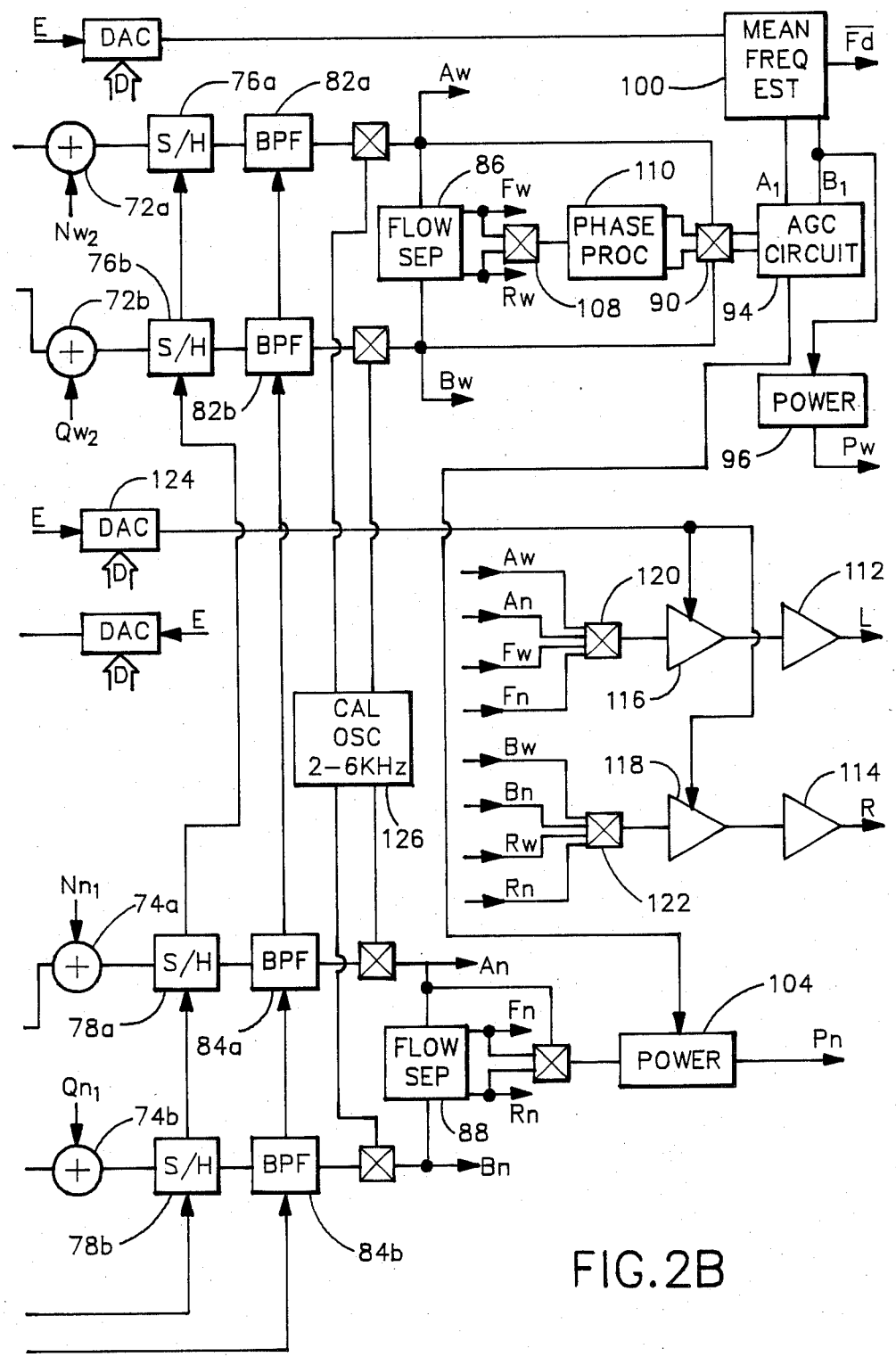

With reference to FIGS. 1 and 2, an apparatus embodying features of the present invention is diagrammatically illustrated. In conjunction with the principles on which the present invention is based, the subject matter found in U.S. Pat. No. 4,067,236 to Hottinger is incorporated herein by reference.

Figure 4:
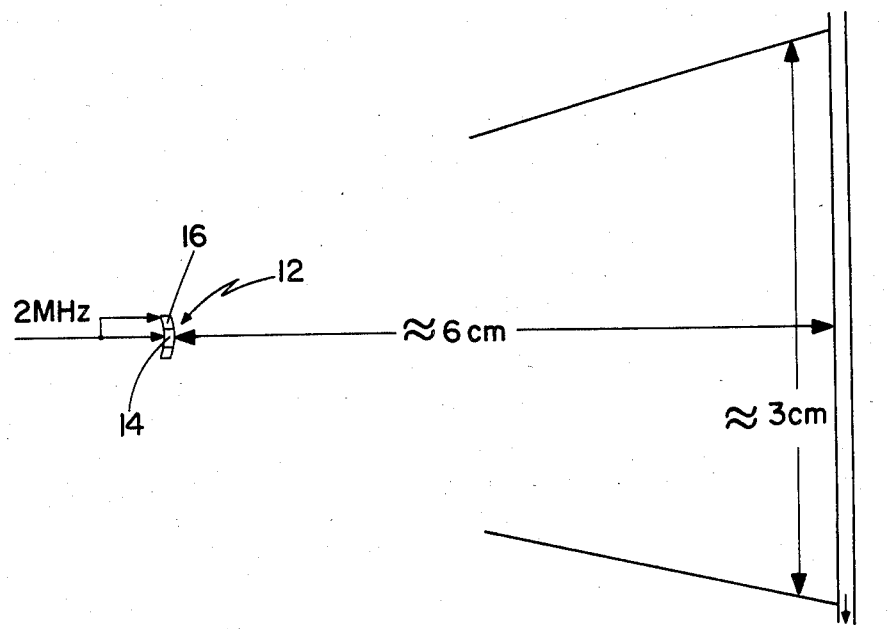
FIG. 4 illustrates a two transducer embodiment for generating a beam of about 3 cm in width about 6 cm from the face of the two transducers.
Figure 5:
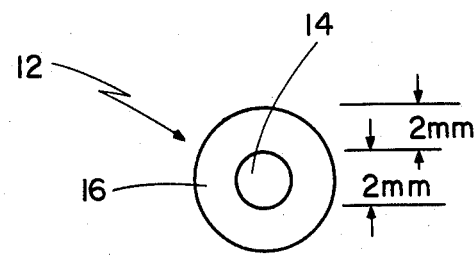
FIG. 5 illustrates an enlarged view of the front face of the two transducer embodiment illustrated in FIG. 4.

The apparatus includes a probe assembly 10 including a transducer 12 for use in transmitting and receiving ultrasonic energy. In the embodiment illustrated, the transducer 12 includes an inner element 14 and an outer element 16 for use in transmitting to and receiving energy from a lumen area 18. In one preferred embodiment, as illustrated in FIGS. 4 and 5 the inner element 14 is a disk having a diameter of about 2 mm and the outer element 16 is a ring or annulus having a width of about 2 mm and being located about the outer periphery of the disk-shaped inner element 14. In this configuration, there is a very small gap between the inner and outer elements 14, 16 so that the two elements are able to operate independently. With this transducer construction, when a 2 MHz signal is applied to the inner and outer transducer elements, a uniform beam of about 3 cm in width is generated about 6 cm from the face of the transducer 12. This configured transducer 12 has particular utility in measuring volume blood flow in the ascending aorta when it is insonated from the suprasternal notch. Other particularly configured transducers can be provided for use in the present invention and the construction of the transducer depends upon the part of the body to be insonified.

The apparatus also includes a clock signal assembly 20, which communicates with the probe assembly 10. The clock signal assembly 20 is used to provide a number of clock or oscillating signals at a predetermined frequency and in which at least certain of the clock signals have a desired phase relationship relative to each other. The clock signal assembly 20 is controlled by a processing/controlling unit 22. The processing/controlling unit 22 is programmable and includes the necessary hardware and software for controlling the operation of the clock signal assembly 20, as well as other parts of the apparatus in determining volume blood flow.

With particular reference to FIG. 2, the clock signal assembly 20 includes a 2 MHz maser oscillator 24, the output of which is applied to a number of clock selectors (CS) 26, 28. In a preferred embodiment, the 2 MHz master clock oscillator is derived from a 16 MHz master oscillator, i.e., the 16 MHz signal is divided down by appropriate logic to provide a desired number of clock signals having different phases thereby resulting in the generation of accurate phase quadrature signals. Each of the clock selectors 26, 28 is controlled by a data input from the processing/controlling unit 22. In connection with energizing the inner element 14 of the transducer 12, clock selector 26 is provided and, with respect to the outer transducer element 16, clock selector 28 is provided. The output of each clock selector 26, 28 communicates with an And gate 30, 32, respectively. The output of the And gate 30 is received by amplifier 34 while the output of the And gate 32 is inputted to amplifier 36. The gain of each of the two amplifiers is controlled by a digital-analog converter (DAC) 38 or 40, with the output of the DAC 38 controlling the gain of the amplifier 34 and the output of the DAC 40 controlling the gain of the amplifier 36. The overall gain of the apparatus is controlled by means of a DAC 42. As can be seen in FIG. 2, the output of the amplifier 34 communicates with and energizes the inner transducer element 14 and the output of the amplifier 36 communicates with and energizes the outer transducer element 16.

The clock signal assembly 20 further includes receiving amplifiers 46, 48. The amplifier 46 communicates with the inner transducer element 14 and amplifies the signal representing returned ultrasonic energy received by this transducer element from the insonified lumen area 18, while the amplifier 48 amplifies the signal representing returned ultrasonic energy received by the outer transducer element 16 from the insonified lumen area 18. The outputs of the amplifiers 46, 48 are applied to demodulating circuitry 50 and direction discriminating circuitry 52. The output signals from the amplifiers 46, 48 can be defined or characterized as wide beam signals or narrow beam signals. The wide beam signals represent a wide beam of ultrasonic energy returned from the insonified lumen area 18 and the narrow beam signals represent narrow beam of ultrasonic energy returned from the insonified lumen area 18.

The clock assembly 20 further includes eight clock selectors 56a-56d and 58a-58d. The clock selectors 56 are associated with wide beam signals and the clock selectors 58 are associated with narrow beam signals, as will be subsequently explained. Each of the outputs of the clock selectors 56, 58 is a clock or oscillating signal and, in the embodiment shown, the clock selectors 56, 58 communicate with the master oscillator 24 to output a 2 MHz signal, with at least some of the outputted clock signals having a phase different from other of the clock signals. The clock signal outputs are also applied to the demodulating circuitry 50 and the direction discriminating circuitry 52.

The demodulating circuitry 50 is used to obtain Doppler signal information from the inputted signals representing the returned ultrasonic energy. The direction discriminating circuitry 52 also receives wide beam and narrow beam signals and is used in determining the direction of blood flow through the lumen area 18 with reference to the probe assembly 10. In particular, it is worthwhile to know whether the blood flow is towards the probe assembly 10 or away from the probe assembly 10. Such a determination enables the operator, for example, to know whether the blood vessel of interest is an artery or a vein. It should be noted that, although the direction discriminating circuitry 52 is identified separately from the demodulating circuitry 50, phase quadrature signals are also involved in the demodulating steps and the demodulating circuitry 50 essentially includes the direction discriminating circuitry 52.

As illustrated in FIG. 2, the demodulating circuitry 50 and the direction discriminating circuitry 52 include a number of multiplier circuits 60, 62, with the multiplier circuits 60a-60d being associated with or responsive to wide beam signals and the multiplier circuits 62a-62d being associated with or responsive to signals representative of the narrow beam. Also inputted to each of the multiplier circuits 60, 62 is a clock signal. The mixing of the returned beam signals and the clock signals results in signals being outputted from the multiplier circuits 60, 62 which are the sums and differences of the frequencies of the signals inputted thereto. As can be seen in FIG. 2, eight circuit channels are provided with four of the circuit channels being associated with the wide beam and four channels being associated with the narrow beam. Two of the wide beam associated channels develop normal signals representative of the wide beam while two of these channels develop quadrature signals, which are 90° out of phase relative to their respective normal signals. That is, the quadrature wide beam signal outputted by the multiplier circuit 60b has the same signal information as that outputted by the multiplier circuit 60a but is 90° out of phase. Similarly, there are four multiplier circuits 62 associated with the narrow beam with two normal signals being outputted by the multiplier circuits 62a, 62c while quadrature signals are found at the outputs of the multiplier circuits 62b, 62d. Like the wide beam signals, the quadrature signal outputted by the multiplier circuit 62b includes the sums and differences of the frequencies of the signals applied thereto and is 90° out of phase relative to the output of the multiplier circuit 62a.

Each of the normal and quadrature signals representative of the received wide beam and the received narrow beam is applied to an amplifier 66, 68. In particular, the amplifiers 66a–66d receive either normal or quadrature signals representative of the wide beam while the amplifiers 68a–68d receive normal or quadrature signals representative of the narrow beam. The gain of each of the amplifiers 66, 68 can be controlled using one of the data latches (DL) 70. The output of each DL 70 is controlled using the processing/controlling unit 22. The amplified normal and quadrature signals are applied to adder circuits 72, 74. The normal signal outputted by the amplifier 66a and representative of the wide beam signal received by the inner transducer element 14 is combined in the adder circuit 72a with the amplified signal from the amplifier 66c, which is representative of the wide beam received by the outer transducer element 16. The adder circuit 72b combines the quadrature signals of these two wide beam related signals. Similarly, the adder circuit 74a receives as its inputs the normal signal from the amplifier 68a, which is representative of the narrow beam received by the inner transducer element 14 for combining it with the amplified signal from the amplifier 68c, which is representative of the narrow beam portion received by the outer transducer element 16. The adder circuit 74b receives the quadrature signals associated with the narrow beam. At the outputs of the adder circuits 72, 74, normal and quadrature signals remain that are separately representative of the wide beam and the narrow beam and include Doppler signal information, which is to be further processed.

In that regard, the demodulating circuitry 50 includes sample-and-hold circuits 76, 78. The sample-and-hold circuit 76a receives the normal wide beam signal outputted by the adder circuit 70a; the sample-and-hold circuit 76b receives the quadrature wide beam signal from the adder circuit 70b; the sample-and-hold circuit 78a receives the normal narrow beam signal from the adder circuit 72a; and the sample-and-hold circuit 78b receives the quadrature narrow beam signal from the adder circuit 72b. Each of the outputs of the sample-and-hold circuits 76, 78 is controlled using the processor/controlling unit 22. Each sample-and-hold circuit 76, 78 is adjusted or controlled in order to output narrow and wide beam signal information that represents a desired, predetermined depth associated with the returned ultrasonic energy, as is well known in the art. The outputs of the sample-and-hold circuits 76, 78 are applied to four band pass filters (BPF) 82, 84. The normal and quadrature signals associated with the wide beam are sent to the band pass filters 82a, 82b while the normal and quadrature narrow beam signals are transmitted to the band pass filters 84a, 84b. Each of the band pass filters filters the signals inputted thereto and outputs Doppler signal information or a Doppler power spectrum.

The normal and quadrature Doppler signals are then applied to flow separator circuits 86, 88, which are used in determining the direction of flow of the blood or fluid being insonified. As depicted in FIG. 2, the flow separator circuit 86 receives normal and quadrature Doppler signals associated with the wide beam and outputs a signal indicative of whether the flow is in a forward direction (Fw) in which the blood or fluid is moving towards the probe assembly 10 or a reverse direction (Rw) in which the blood or fluid is moving in a direction away from the probe assembly 10. Similarly, the flow separator circuit 88 receives the normal and quadrature Doppler signals associated with the narrow beam and outputs signals Fn and Rn indicative of whether the flow is in a forward or reverse direction, respectively.

In addition to being applied to the flow separator circuit 86, the normal and quadrature signals associated with the wide beam are applied to a switch 90, which communicates with an AGC circuit 94. Because the normal and quadrature Doppler signals widely fluctuate in amplitude, it has been found necessary to utilize the AGC circuit 94 in order to reduce the fluctuations and to provide a more constant or consistent output, as will be explained in greater detail in connection with a discussion of the operation of the apparatus.

To determine the necessary information for calculating the volume blood flow, the Doppler power spectrum or Doppler signal information associated with the wide beam is outputted from the AGC circuit 94 to a power measuring device 96 and also to a mean frequency estimator circuit 100. The power measuring device 96 is a well-known circuit and outputs a signal representative of the power in the wide beam, as discussed in the '236 patent to Hottinger. The mean frequency estimator circuit 100 is a conventional implementation of a circuit for determining the mean frequency (Fd) of the Doppler power spectrum inputted thereto, in accordance with the principles disclosed in the Hottinger patent. The mean frequency is directly related to the velocity of the blood flowing through the insonified lumen area 18.

Referring back to the narrow beam channels or section of the apparatus, the normal and quadrature Doppler signals associated with the narrow beam are applied to a switch 102. Also inputted to the switch 102 are narrow beam signals indicative of whether the flow is in a forward (Fw) or reverse direction (Rw). The output of the switch 102 is sent to the power measuring device 104 for the narrow beam. The power measuring device 104 is comparable to the power measuring device 96 and outputs a signal representative of the power in the Doppler power spectrum associated with the narrow beam. Also operatively associated with the power measuring device 104 is a feedback control signal generated by the AGC circuit 94. This control signal is used to avoid inaccuracies in determining the ratio of Pw to Pn, as will be subsequently explained in greater detail. Each of the determined outputs Fd, Pw, and Pn are inputted to the processing/controlling unit 22 for use in determining the volume blood flow of the insonified lumen area 18. In connection with receiving the mean frequency Fd, the processing/controlling unit 22 utilizes the determined magnitude of Fd to calculate flow velocity of the blood or fluid and output the same to a recording device 106. Consequently, the operator is able to view a flow velocity trace or graph during the time that the probe assembly 10 is positioned at or near a desired part of the body of a patient that receives ultrasonic energy.

As also seen in the wide beam circuit channel of FIG. 2, a switch 108 receives the output from the flow separator circuit 86. The output of the switch 108 is sent to a phase processor 110 for producing a quadrature signal for the signal representing forward flow Fw or the signal representing reverse flow Rw, whichever is applicable. The phase processor 110 outputs normal and quadrature signals associated with the signal then being outputted by the flow separator circuit 86. The normal and quadrature signals from the phase processor 110 are applied to the switch 90, which can be controlled by the operator of the apparatus so that, instead of normal and quadrature signals from the band pass filters 82a, 82b being applied to the AGC circuit 94, the normal and quadrature signals from the phase processor 110 are sent.

With further reference to FIG. 2, the apparatus includes circuitry for use in permitting the operator to listen to the returned Doppler signal information. In particular, left and right signal outputs are generated for input to a loud speaker or earphones so that the operator is able, under switch control, to listen to selected signals representative of the Doppler information found in the returned wide and narrow beams of ultrasonic energy, including both normal and quadrature signals, as well as the flow separated signals outputted from the flow separator circuits 86, 88. The amplifier 112 outputs the left output signal and the amplifier 114 outputs the right output signal. A pair of amplifiers 116, 118 amplify the input signal applied thereto from operator-controlled switches 120, 122, respectively. The gain of each of the amplifiers 116, 118 is controlled using the processing/controlling unit 22 and a DAC 124.

Lastly, in the preferred embodiment, the apparatus includes a calibration oscillator 126, which is capable of outputting one of a number of signals having a predetermined frequency. Preferably, the outputted signal is in the range of 2-6 KHz. The calibration oscillator 126 is used in calibrating and checking the accuracy of the power measuring device 96, mean frequency estimator circuit 100, and power measuring device 104, as well as hardware and software of the processing/controlling unit 22.

With respect to the operation of the apparatus, the probe assembly 10 is placed on or near the patient's skin at a position to suitably insonify a desired lumen area 18. The operator of the apparatus also locates the recording device 106 in a position that permits easy observation of the flow velocity trace. Upon activation by the operator and under the control of the processing/controlling unit 22, clock signals are transmitted, via the And gates 30, 32 to the amplifiers 34, 36. A transmitted wide beam of energy is generated by applying amplified clock signals to the inner and outer transducer elements 14, 16. In the preferred embodiment, the wide beam is produced by clock signals simultaneously applied to the inner and outer transducer elements 14, 16, with the signal applied to the outer transducer element 16 being 180° out of phase relative to the signal applied to the inner transducer element 14. The transmitted wide beam of energy is received by the lumen area 18 of interest and some of the ultrasonic energy contacted by the lumen area and the red corpuscles of blood is reflected back to the probe assembly 10. The returned ultrasonic energy is simultaneously received by both the inner and outer transducer elements 14, 16. During the time associated with the reception of reflected ultrasonic energy, the processing/controlling unit 22 prevents the transmission of ultrasonic energy to the lumen area 18. Consequently, there is a predetermined time for transmitting ultrasonic energy and a different predetermined time for receiving reflected ultrasonic energy so that no overlap is created.

With regard to the returned ultrasonic energy, wide and narrow beam signals, comprising the sums and differences of the signal frequencies, are produced using the clock selectors 56, 58 and the multiplying circuits 60, 62. A signal representative of the wide beam includes outputs from the inner and outer transducer elements 14, 16, with the outputs being 180° out of phase. The electrical representation of the returned narrow beam also includes signals outputted by both the inner and outer transducer elements 14, 16, but with these signals being substantially in phase. At the same time, both signals representative of the wide beam and the narrow beam, including generated quadrature signals, are demodulated by the demodulating circuitry 50 with the quadrature signal generating circuitry forming part of the direction discriminating circuitry 52 for use in determining the direction of blood flow in the insonified lumen area 18.

As the signals, including Doppler information, pass through the demodulating circuitry 50, the two sets of signals, normal and quadrature signals generated using the outputs from the two transducer elements 14, 16, representative of the wide beam are combined and the two sets of signals representative of the narrow beam are also combined. Under control of the processing/controlling unit 22, the sample-and-hold circuits 76, 78 output wide and narrow beam signals providing information for the desired depth associated with the lumen area 18 being insonified. The band pass filters 82, 84 of the wide and narrow beam channel circuits, each having a band pass controllable by the processing/controlling unit 22, pass signals having a frequency corresponding to the frequency difference between the transmitted ultrasonic energy and the received ultrasonic energy so that normal and quadrature Doppler signals or Doppler power spectrums are outputted by the filters 82, 84.

Figure 3:
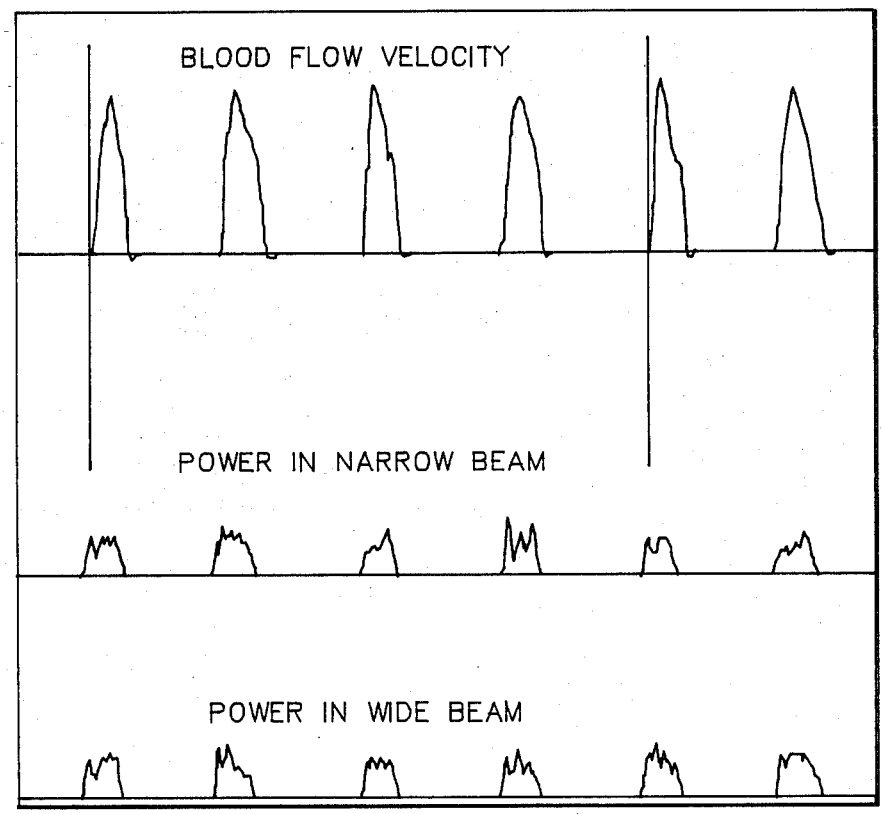
FIG. 3 illustrates a graphic representation or data printout relating to blood flow from a typical adult including a flow velocity trace and traces of wide beam and narrow beam power.

The normal and quadrature Doppler signals representative of the wide beam are sent to the AGC circuit 94 where unwanted amplitude fluctuations are removed. Because the ratio of Pw to Pn is found in determining volume blood flow, it is necessary that no inaccuracy occur in this result due to the adjustment by the AGC circuit 94 of the normal and quadrature Doppler power spectrums associated with the wide beam. This is accomplished by using the same control signal, developed by the AGC circuit 94 for controlling the amplitude fluctuations in the wide beam Doppler signals, to control the amplitudes of the narrow beam Doppler signals. Since the ratio of the two powers is obtained, modifying Doppler signals associated with the wide beam and also those associated with the narrow beam, avoids the introduction of an inaccuracy because of the use of the AGC circuit 94. For example, if the Doppler power associated with the wide beam increases, then the AGC circuit 94 compensates by decreasing its control voltage, which in turn, reduces the level of the Doppler power associated with the narrow beam. This has an overall effect of keeping the power signal associated with the wide beam at a constant level but varies the power level in the narrow beam. In the case in which the Doppler power in the wide beam increases, which occurs when there is a large flow lumen area 18, then the Doppler power in the wide beam will remain substantially constant but the control voltage from the AGC circuit 94 will reduce the Doppler power associated with the narrow beam. The overall effect is the same since the ratio of Pw to Pn is taken and, although the Doppler power associated with the wide beam has been held substantially constant, the ratio of the power in the wide beam to the power in the narrow beam increases because the Doppler power associated with the narrow beam has been reduced. For each of the power measuring devices 96, 104, the Doppler power spectrum associated with each of the respective narrow and wide beams is processed to determine Pw and Pn. The Doppler power spectrum associated with the wide beam after being adjusted in amplitude, is also used to determine the mean frequency (Fd) thereof by means of the mean frequency estimator circuit 100. The processing/controlling unit 22 receives the mean frequency and determines the flow velocity of the blood through the insonified lumen area 18. Signals representative of the flow velocity at each instance in time are applied to the recording device 106 so that the operator is able to view a trace of the blood flow velocity. With reference to FIG. 3, the top graph is a representative flow velocity trace of blood flow from the heart of a typical adult. In addition to flow velocity, the magnitudes of the determined powers Pw and Pn are inputted to the processing/controlling unit 22, which develops signals for input to the recording device 106 whereby wide beam power and narrow beam power traces are also provided. In the preferred embodiment, the operator also selects one of the available inputs to the left and right signal outputs and listens to the Doppler signals using the loud speaker or earphones.

Before relying on a calculation of the volume blood flow by the processing/controlling unit 22, the operator checks the flow velocity and power traces on the recording device 106, as well as the sounds associated with the Doppler information found in the left and right output signals. In the case of the flow velocity trace, the operator determines whether the amplitudes of the periodic signals are substantially at a maximum and have a substantially consistent amplitude. When this occurs, the operator knows that the probe assembly 10 and the transducer 12 are properly located for insonifying the desired lumen area 18. If the flow velocity trace did not provide such an indication, the position of the probe assembly 10 is changed until the known flow velocity trace is realized.

Upon achieving desired positioning of the probe assembly 10 and an expected flow velocity trace, an accurate determination of volume blood flow can be made since the values of the mean frequency and the powers in the wide and narrow beams are at their most accurate levels for the desired, insonified lumen area 18. The calculation of volume blood flow associated with the lumen area 18 is made by the processing/controlling unit 22 and a visual representation of the determined magnitude can be provided on the recording device 106 in units of liters/minute.

It should be appreciated that a number of modifications can be made to the present invention without departing from the inventive subject matter. First, although quadrature signals are generated for both narrow and wide beam signals, it is only necessary to generate quadrature signals for one of the two beams in order to determine the direction of flow. Second, the AGC circuit could be responsive to Doppler signals associated with the narrow beam and a control signal developed to modify the Doppler signals associated with the wide beam. However, it has been found that greater sensitivity is achieved by positioning the AGC circuit in the wide beam circuit channel. Although the quadrature signal associated with the wide beam is illustrated in FIG. 2 as the input to the power measuring device for the wide beam, the normal signal outputted by the AGC circuit could be used in determining the power associated with the wide beam. Further changes could be made to the embodiment of FIG. 2 without affecting the operability of the novel aspects of the present invention.

Based on the detailed description, a number of meaningful advantages of the present invention are immediately discerned. An apparatus for measuring volume blood or fluid flow is provided which can be readily operated in a clinical environment. The particular implementation disclosed herein results in an accurate determination of volume blood flow because of the simultaneous processing of narrow beam and wide beam signal information and proper placement of the probe assembly due to the ability to observe a trace of blood flow velocity. In addition, unwanted amplitude fluctuations in the Doppler power spectrum are removed without jeopardizing the determination of the power associated with the wide and narrow beams. Further, a preferably constructed transducer is disclosed for generating a wide uniform beam of ultrasonic energy for monitoring and measuring volume blood flow through the ascending aorta. The apparatus also incorporates an effective way for determining the direction of fluid flow.

What is claimed is:

1. A method for use in measuring volume fluid flow, comprising:
   providing transducer means having a plurality of transducer elements;
   locating said transducer means in a position for monitoring the flow of fluid through vessel means;
   transmitting ultrasonic energy directed towards the vessel means using said transducer means;
   receiving returned ultrasonic energy from the flowing fluid using said transducer means wherein a wide beam of returned ultrasonic energy and a narrow beam of returned ultrasonic energy are defined;
   developing signals representative of said wide beam and said narrow beam;
   processing said signals to provide a Doppler power spectrum associated with each of said wide beam and said narrow beam;

controlling signal amplitudes of said Doppler power spectrum associated with one of said wide beam and said narrow beam wherein said signal amplitudes are controlled at a substantially constant level;

generating a control signal using said Doppler power spectrum associated with one of said wide beam and said narrow beam; and controlling signal amplitudes of the other of said Doppler power spectrums associated with said wide beam and said narrow beam using said control signal, wherein said signal amplitudes of said other of said Doppler power spectrums are not controlled at a substantially constant level whereby the ratio between said Doppler power spectrum associated with said wide beam and said Doppler power spectrum associated with said narrow beam is accurately maintained by reducing the level of said Doppler power spectrum associated with one of said narrow beam and said wide beam when there is an increase in said Doppler power spectrum associated with said other of said narrow beam and said wide beam.

2. A method, as claimed in claim 1, wherein:
said generating step includes obtaining said control signal using said Doppler power spectrum associated with said wide beam.

3. A method, as claimed in claim 1, further including:
determining the power associated with each of said wide beam and said narrow beam and calculating the ratio of said wide beam power and said narrow beam power.

4. A method, as claimed in claim 1, further including:
determining the mean frequency associated with said Doppler spectrum of one of said wide beam and said narrow beam and using said mean frequency to determine flow velocity of the fluid.

5. A method, as claimed in claim 4, further including:
providing a visual representation of said flow velocity, observing said flow velocity, and making an accurate determination of volume fluid flow in the vessel means after a known, predetermined representation of said flow velocity is observed.

6. A method, as claimed in claim 1, wherein:
said processing step includes processing signals representative of said wide beam at the same time signals are being processed representative of said narrow beam.

7. A method, as claimed in claim 1, wherein:
said transducer means includes an outer element and an inner element and said wide beam is defined by a first signal component generated using said inner element and a second signal component using said outer element, said first and second signal components being out of phase.

8. A method, as claimed in claim 7, wherein:
said narrow beam is defined by a first signal component generated using said inner element and a second signal component generated using said outer element, said first and second signal components being substantially in phase.

9. A method, as claimed in claim 1, further including:
generating a plurality of quadrature signals using oscillator signals and returned ultrasonic energy.

10. A method, as claimed in claim 9, wherein:
said plurality of quadrature signals includes two quadrature signals associated with said wide beam and two quadrature signals associated with said narrow beam.

11. A method for use in measuring volume fluid flow, comprising:

providing transducer means having a first transducer element and a second transducer element;

locating said transducer means in a position for monitoring the flow of fluid through vessel means;

transmitting ultrasonic energy directed towards the vessel means using said transducer means;

generating a first signal component using said first transducer element of said transducer means and returned ultrasonic energy;

generating a second signal component using said second transducer element of said transducer means and returned ultrasonic energy, said first and second signal components being out of phase;

combining said first and second signal components to provide a wide beam signal representative of a wide beam;

generating a third signal component using said first transducer element of said transducer means and returned ultrasonic energy;

generating a fourth signal component using said second transducer element of said transducer means and returned ultrasonic energy, said third and fourth signal components being substantially in phase;

combining said third and fourth signal components to generate a narrow beam signal representative of a narrow beam, said generating of said wide beam signal and said narrow beam signal occurring at substantially the same time wherein an accurate determination of the ratio of the powers associated with said wide and narrow beams can be subsequently made;

maintaining said wide beam signal and said narrow beam signal in separate circuit channels to subsequently determine the power associated with each of said wide beam and said narrow beam;

determining separately a value relating to the power associated with said wide beam using said wide beam signal and a value relating to the power associated with said narrow beam signal; and after separately obtaining said power values, using each of said power values in determining the volume fluid flow.

12. A method, as claimed in claim 11, further including:
generating at least one quadrature signal associated with one of said wide beam and said narrow beam.

13. A method, as claimed in claim 11, further including:
providing a visual representation of flow of the fluid;
observing said visual representation of said flow of the fluid; and
outputting an accurate determination of volume fluid flow after observing that the visual representation of the fluid flow corresponds to a known, predetermined representation indicating that said transmitted ultrasonic energy is being transmitted by the vessel means at a desired location.

14. A method, as claimed in claim 11, wherein:
said providing of said transducer means includes having said second transducer element concentrically located relative to said first transducer element and said transmitting of said ultrasonic energy includes energizing said first transducer element using a first signal and energizing said second transducer element using a second signal, said second signal being out of phase relative to said first signal.

15. A method, as claimed in claim 14, wherein:
said second signal is substantially 180° out of phase relative to said first signal.

16. A method, as claimed in claim 11, wherein:
said providing of said transducer means includes having said second transducer element concentrically located relative to said first transducer element, said transmitting of said ultrasonic energy includes energizing both said first and second transducer elements.

17. An apparatus for use in measuring volume fluid flow, comprising:
transducer means having a first transducer element and a second transducer element, said transducer means for transmitting ultrasonic energy in a direction towards a vessel means containing moving fluid and for receiving returned ultrasonic energy from the moving fluid, said transducer means being used to define a wide beam of returned ultrasonic energy and a narrow beam of returned ultrasonic energy and for developing signals representative of said wide beam and said narrow beam;
means for processing said signals to output a Doppler power spectrum associated with each of said wide beam and said narrow beam;
means for determining the power in said wide beam and in said narrow beam using each of said Doppler power spectrums;
means for calculating the ratio between said wide beam power and said narrow beam power; and
means for controlling signal amplitudes of said narrow beam, said signal amplitudes of said one of said wide beam and said narrow beam being controlled at a substantially constant level and at least portions of said means for controlling used in controlling signal amplitudes of the other of said Doppler power spectrums of said wide beam and said narrow beam, wherein said signal amplitudes of said other of said Doppler power spectrums are not controlled at a substantially constant level whereby the ratio between said Doppler power spectrum associated with said wide beam and said Doppler power spectrum associated with said narrow beam is accurately maintained by reducing the level of said Doppler power spectrum associated with one of said narrow beam and said wide beam when there is an increase in said Doppler power spectrum associated with said other of said narrow beam and said wide beam.

18. An apparatus, as claimed in claim 17 herein:
said one of said wide beam and said narrow beam is said wide beam.

19. An apparatus, as claimed in claim 17, wherein:
said means for processing includes means for providing a 2 MHz signal and wherein said first element is an outer ring having a width of about 2 mm and said transmitted beam has a width of about 3 cm at a distance of about 6 cm from said transducer means.

20. An apparatus, as claimed in claim 17, wherein said means for processing includes:
first circuit channel means associated with said wide beam; and
second circuit channel means associated with said narrow beam, said first and second circuit channel means processing Doppler signal information at the same time for use in determining the power in said wide beam at the same time said power in said narrow beam is determined.

21. An apparatus, as claimed in claim 17, wherein:
said means for processing includes means for generating a plurality of quadrature signals, at least two of said quadrature signals being associated with one of said wide beam and said narrow beam.

22. An apparatus, as claimed in claim 17, wherein said means for processing includes:
means for generating a first clock signal for combining with a signal outputted by said first transducer element and associated with said wide beam;
means for generating a second clock signal for combining with a signal outputted by said second transducer element and associated with said wide beam;
means for generating a third clock signal for combining with a signal outputted by said first transducer element and associated with said narrow beam; and
means for generating a fourth clock signal for combining with a signal outputted by said second transducer element and associated with said narrow beam, and wherein each of said first, second, third and fourth clock signals are being combined at substantially the same time with their respective signals from said transducer means.

23. An apparatus, as claimed in claim 17, wherein:
said means for processing includes calculating means for determining volume fluid flow using said mean frequency and said power ratio.

24. An apparatus for use in measuring volume fluid flow, comprising:
transducer means including a first transducer element and a second transducer element, said transducer means for transmitting ultrasonic energy directed towards a vessel means and receiving ultrasonic energy from the vessel means;
means for generating a first signal component using said first transducer element of said transducer means and returned ultrasonic energy;
means for generating a second signal component using said second element of said transducer means and returned ultrasonic energy, said first and second signal components being out of phase;
means for generating a third signal component using said first element of said transducer means and returned ultrasonic energy;
means for generating a fourth signal component using said second element of said transducer means and returned ultrasonic energy, said third and fourth signal components being substantially in phase;
means for combining said first and second signal components to generate a wide beam signal representative of a wide beam;
means for combining said third and fourth signal components to generate a narrow beam signal representative of a narrow beam, said wide beam signal and said narrow beam signal being generated at substantially the same time wherein an accurate determination of the ratio of the powers associated with the wide and narrow beams can be subsequently made and wherein said wide beam signal and said narrow beam signal are generated in separate circuit channels to subsequently determine the power associated with each of said wide beam and said narrow beam;
means for determining the power in said wide beam;

means for determining, separately from the determination of the power in said wide beam, the power in said narrow beam;

means for determining a mean frequency associate one of said wide beam and said narrow beam;

means for calculating the ratio between said wide beam power and said narrow beam power; and means for determining volume fluid flow using said mean frequency and aid ratio between said wide beam power and said narrow beam power.

25. An apparatus, as claimed in claim 24, wherein:

said first transducer element is in the shape of a disk having a diameter of about 2 mm; and said second transducer element is positioned outwardly of said first transducer element and is substantially concentric relative to aids first transducer element, said second transducer element being in the shape of a ring having a width of about 2 mm and, when each of said first and second transducer elements is energized using about a 2 MHz signal, said transducer means transmits a relatively uniform beam of ultrasonic energy having a width of about 3 cm at a distance of about 6 cm form said transducer means.

* * * * *